United States Patent
Livney

(10) Patent No.: US 11,173,127 B2
(45) Date of Patent: Nov. 16, 2021

(54) POTATO PROTEIN NANOPARTICLES

(71) Applicant: Technion Research & Development Foundation Limited, Haifa (IL)

(72) Inventor: Yoav D. Livney, Misgav (IL)

(73) Assignee: TECHNION RESEARCH & DEVELOPMENT FOUNDATION LIMITED, Haifa (IL)

( * ) Notice: Subject to any disclaimer, the term of this patent is extended or adjusted under 35 U.S.C. 154(b) by 295 days.

(21) Appl. No.: 15/021,964

(22) PCT Filed: Sep. 17, 2014

(86) PCT No.: PCT/IL2014/050832
§ 371 (c)(1),
(2) Date: Mar. 15, 2016

(87) PCT Pub. No.: WO2015/040616
PCT Pub. Date: Mar. 26, 2015

(65) Prior Publication Data
US 2016/0220502 A1 Aug. 4, 2016

(30) Foreign Application Priority Data

Sep. 17, 2013 (IL) .......................................... 228528

(51) Int. Cl.
*A61K 9/51* (2006.01)
*A61K 9/00* (2006.01)
*A61K 31/59* (2006.01)

(52) U.S. Cl.
CPC .......... *A61K 9/5169* (2013.01); *A61K 9/0095* (2013.01); *A61K 31/59* (2013.01)

(58) Field of Classification Search
CPC ..... A61K 9/0095; A61K 9/5169; A61K 31/59
See application file for complete search history.

(56) References Cited

U.S. PATENT DOCUMENTS

| | | | | |
|---|---|---|---|---|
| 6,290,974 | B1 * | 9/2001 | Swaisgood | A21D 2/263 424/401 |
| 8,465,911 | B2 * | 6/2013 | Giuseppin | A23L 2/66 435/4 |
| 2010/0040591 | A1 * | 2/2010 | Giuseppin | A23J 1/006 424/94.1 |
| 2012/0288533 | A1 | 11/2012 | Livne | |

FOREIGN PATENT DOCUMENTS

| | | |
|---|---|---|
| EP | 2625966 A1 | 8/2013 |
| WO | 9900113 A1 | 1/1999 |
| WO | 2009137112 A1 | 11/2009 |
| WO | 2012089666 A1 | 5/2012 |

OTHER PUBLICATIONS

Ralet et al. "Fractionation of Potato Proteins: Solubility, Thermal Coagulation and Emulsifying Properties" (2000) Lebensm. Wiss. u-Technol. vol. 33: 380-387.*
Romero et al. "Interfacial and Oil/Water Emulsions Characterization of Potato Protein Isolates" (2011) American Chemical Society, vol. 59: 9466-9474.*
National Sunflower Assocaiton "Facts About Vitamin E" (2003) NSA, available at https://www.sunflowernsa.com/health/vitamin-e/ (last accessed Feb. 19, 2018).*
Van Koningsveld, "Effects f Protein Composition and Enzymatic Activity on Formation and Properties of Potato Protein Stabilized Emulsions" (2006), J. Agric. Food Chem. vol. 54: 6419-6427. (Year: 2006).*
International Search Report from a counterpart foreign application—PCT/IL2014/050832—3 pages, dated Jan. 19, 2015.
Written Opinion of the International Search Authority from a counterpart foreign application—PCT/IL2014/050832—4 pages, dated Jan. 19, 2015.
Gruppen et al. (2012) Protein Concentration and Protein-Exposed Hydrophobicity as Dominant Parameters Determining the Flocculation of Protein Stabilized Oil-in-Water Emulsions, Langmuir (8 pages).
Schäfer D. et al. (2018) Mechanical and Barrier Properties of Potato Protein Isolate-Based Films. Coatings 2018, 8, 58: doi:10.3390/coatings 8020058—16 pages.
Delahaije et al. (2013) Protein Concentration and Protein-Exposed Hydrophobicity as Dominant Parameters Determining the Flocculation of Protein Stabilized Oil-in-Water Emulsions, Langmuir (8 pages).

* cited by examiner

*Primary Examiner* — Teresa E Knight
(74) *Attorney, Agent, or Firm* — The Roy Gross Law Firm, LLC; Roy Gross

(57) ABSTRACT

This invention provides a nanoparticle made of: a potato protein; and a bioactive compound bound to the potato protein. The invention further provides foods or beverages, including clear ones, which are supplemented with the nanoparticles made of: a potato protein; and a hydrophobic bioactive compound bound to the potato protein. The process of making the nanoparticles of the invention, and methods for supplementing foods or beverages with hydrophobic bioactive compounds via the nanoparticles of the invention and are also provided.

11 Claims, 4 Drawing Sheets

POTATO PROTEIN NANOPARTICLES

FIELD OF INVENTION

This invention is directed to, inter alia, (1) a nanoparticle comprising: a potato protein; and a bioactive compound bound to the potato protein, and (2) beverages or foods supplemented with the nanoparticles.

BACKGROUND OF THE INVENTION

Preventive medicine consists of measures taken to reduce the risk of diseases, including avoiding smoking, performing physical exercises and following prudent dietary recommendations.

Recently, there is an increasing awareness that food may be either harmful or beneficial to health. This is based in part on a growing scientific understanding of the disease-preventive properties of foods, and in particular certain food components, known as nutraceuticals, such as vitamins, omega-3 fatty acids, and certain phytochemicals. Nutraceuticals are health-promoting bioactives. They have been associated with the prevention and/or treatment of disorders like cardio-vascular disease, cancer, hypertension, diabetes, osteoporosis, arthritis etc.

One way to increase the consumption of health promoting bioactives is to enrich foods and beverages that people normally consume with nutraceuticals. However, enriching foods with nutraceuticals may pose great challenges, especially when the nutraceuticals are poorly water-soluble, and are easily degradable.

The solubilization of hydrophobic health-promoting bioactives in clear drinks is highly sought by beverage producers to provide added value for the consumer, but it still poses tough challenges, particularly in shelf stable drinks. Most food grade surfactants, which may be used for the task are synthetic e.g. the Tween (polysorbate) series, and thus preclude an "all-natural ingredients" labeling. Other ways to enrich beverages with hydrophobic nutraceuticals, like gum Arabic, milk proteins, soybean proteins and Maillard reaction conjugates are either expensive, not always available, or are using allergenic components.

Clear drinks, which are consumed in large quantities, pose a particularly important challenge because of the difficulty of incorporating oil-soluble materials in a clear and stable aqueous system. The ideal vehicle for the task should be nano-sized to maintain transparency, preferably ≤100 nm, and comprised of only natural, generally regarded as safe and inexpensive food components, capable of solubilizing and protecting hydrophobic biologically active molecules in aqueous media while retaining sensory qualities, and promoting bioavailability of hydrophobic biologically active molecules. Very few solutions for these challenging requirements have been suggested and none has all the desired attributes.

Potato protein isolates (PPI) are a relatively newly available food ingredient. Particularly native protein isolates which are highly functional, in terms of excellent solubility and good emulsifying and foaming abilities. Potato is a cheap and widely available produce, and its proteins have a high nutritional value compared to most major plant proteins and close to that of egg proteins. Importantly, potato proteins are considered GRAS and non-allergenic and hence are not included in the list of known food allergens, which must be declared on the label—A major advantage for the manufacturer, and a crucial safety requirement for the well-being of consumers.

Nanoencapsulation is a rapidly developing technology which has great potential to overcome solubility limitations, protect sensitive compounds from degradation during production and shelf-life, mask undesired off-flavors, and promote bioavailability of encapsulated nutraceuticals.

Vitamin D and omega 3 were chosen as model hydrophobic nutraceutical compounds. Vitamin D is a fat soluble vitamin that has great importance for calcium and phosphorus homeostasis. VD is also associated with cardiovascular health, cancer prevention, insulin sensitivity, regulation of immune function and decreased risk of autoimmune diseases. Vitamin D3 ($VD_3$) is synthesized in the skin upon exposure to ultraviolet type-B radiation. There are scarce natural dietary sources for VD, including certain fish oils and egg yolk. About 1 billion people worldwide are VD deficient or insufficient, mainly due to avoidance of sun exposure to prevent melanoma, the use of sunscreen which blocks VD synthesis and low dietary intake. Besides its low solubility in water, vitamin D is sensitive to low pH, oxidation and heat.

Omega 3 fatty acids show remarkable preventive-medicine activities: they reduce the risk of cardiovascular diseases and the metabolic syndrome, they lower blood pressure, serum cholesterol and triglyceride levels and they are considered to have antithrombotic, antiatherogenic and anti-inflammatory properties. However, omega 3 fatty acids and their ester forms have very low aqueous solubility, and very high sensitivity to oxidation, resulting in undesired odors.

SUMMARY OF THE INVENTION

In one embodiment, the present invention provides a nanoparticle comprising: (a) a potato protein; and (b) a bioactive compound bound to the potato protein. The bioactive compound, in some embodiments, is a compound having maximal aqueous solubility below 1 g/l. The bioactive compound, in some embodiments, is an oil-soluble vitamin, a polyunsaturated fatty acid or its ester, an antioxidant, a phytochemical, an Omega-3 fatty acid, or its esters, or any combination thereof.

In another embodiment, the present invention further provides a composition comprising an aqueous liquid, a bioactive compound, and a potato protein. In some embodiments, the aqueous liquid is a transparent aqueous liquid such as a clear beverage. In one embodiment, a composition comprising an aqueous liquid, a bioactive compound, and a potato protein is devoid of an additional emulsifier.

In another embodiment, the present invention further provides a method for supplementing a subject with a bioactive compound, comprising the step of administering to the subject a composition comprising: an aqueous liquid, a bioactive compound, and a potato protein bound to the bioactive compound, thereby supplementing a subject with a bioactive compound. In some embodiments, the subject is afflicted with a disease requiring essential fatty acids support such as: a cardiovascular disease, a reproductive disease, an immune disease, a nervous system disease, or any combination thereof.

In another embodiment, the present invention further provides a process for preparing a nanoparticle comprising: a potato protein; and a bioactive compound bound to the potato protein, comprising the steps of preparing a first solution, a second solution, a mix of the first solution and the second solution; wherein the first solution is prepared according to the steps of: (a) dissolving the potato protein in water at a concentration of 0.1 to 100 g/L; (b) stirring the solution obtained in (a) for 20 minutes to 20 hours at 4 to 40°

C.; and (c) filtering the solution obtained in (b) through a filter having a cutoff of 0.1 to 1 microns; wherein the second solution is prepared according to the step of: dissolving the bioactive compound in a water-miscible organic food grade solvent; wherein the mix is prepared according to the step of: combining the first solution and the second solution by slowly adding said second solution into the first solution while intensive stirring is applied, thereby preparing a nanoparticle dispersion comprising: a potato protein; and a bioactive compound bound to the potato protein.

The nanoparticles of the invention may be dried by any method known in the art, with or without the use of drying aids, such as saccharides, and reconstituted in water or aqueous solution to form a clear stable solution or dispersion.

DETAILED DESCRIPTION OF THE INVENTION

Figure 1:
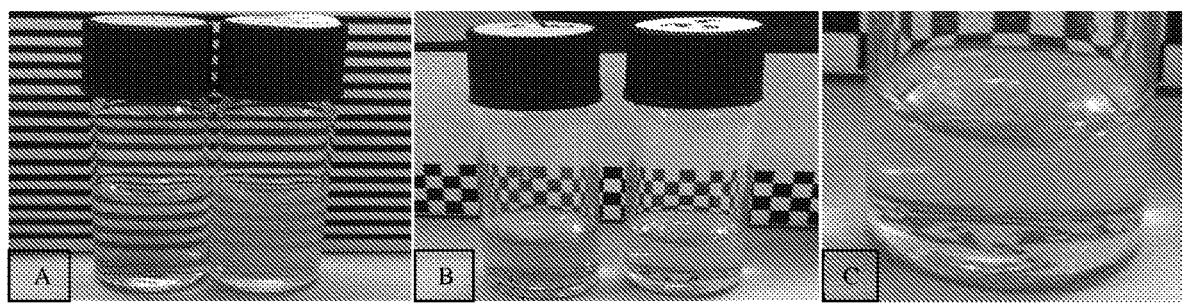
FIG. 1. Is an image showing: A. Effect of potato protein on solubilization of VD and transparency of solutions containing VD: The two aqueous buffer solutions (25 mM phosphate buffer, pH 2.5) contained the same concentration of VD (0.1 mg/ml), but the vial on the left contained also 1.5 mg/ml potato protein. B. Effect of potato protein on solubilization of omega 3 and on transparency of solutions containing omega 3: The two aqueous buffer solutions (25 mM phosphate buffer, pH 2.5) contained the same concentration of omega 3 DHA (ethyl ester) 0.5 ul/ml colored with Nile red, which is only pink in a hydrophobic environment, but the vial on the left contained also 1.5 mg/ml potato protein. C. Magnified view of the floating oil droplets on top of the liquid, and on the walls of the right vial in picture B, devoid of potato protein.
Figure 2:
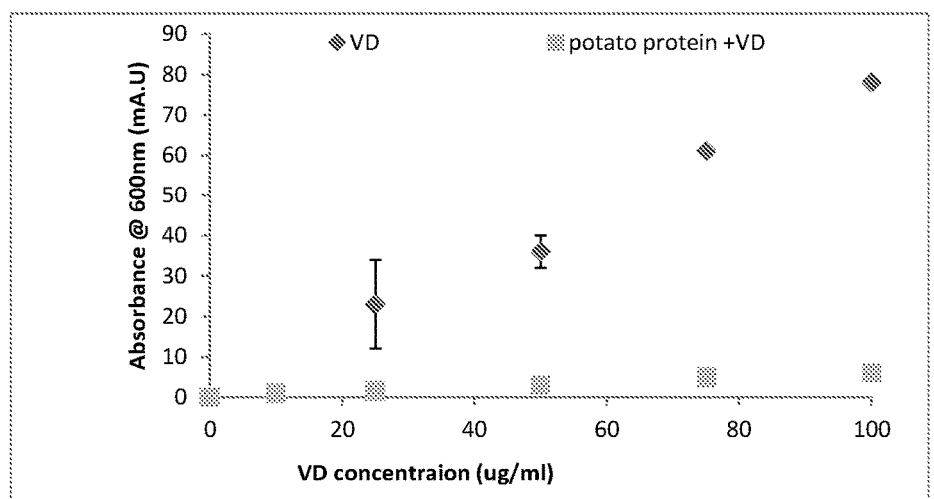
FIG. 2. A graph showing VD turbidity at 600 nm in the presence or absence of potato protein (1 mg/ml), pH 2.5.

In one embodiment, the present invention provides a nanoparticle (or a plurality of nanoparticles) comprising: (a) a potato protein; and (b) a bioactive compound bound to the potato protein. In another embodiment, the present invention further provides that the nanoparticle of the invention is a nanocapsule comprising: (a) a nanoshell comprising a potato protein; and (b) a core comprising a bioactive compound bound to- and encapsulated by the potato protein nanoshell.

In another embodiment, the nanoshell consists a potato protein. In another embodiment, the nanoshell comprises an additional polymer. In another embodiment, the additional polymer is a biodegradable polyester polymer. In another embodiment, the additional polymer is Poly-e-caprolactone (PCL). In another embodiment, the additional polymer is poly(lactide) (PLA). In another embodiment, the additional polymer is poly(lactide-co-glicolide) (PLGA). In another embodiment, the additional polymer is poly(methacrylic acid). In another embodiment, the additional polymer is poly(N-vinyl Pyrrolidone). In another embodiment, the additional polymer is a synthetic polymer. In another embodiment, the additional polymer is a polysaccharide. In another embodiment, the additional polymer is chitosan. In another embodiment, the additional polymer is gelatin. In another embodiment, the additional polymer is sodium alginate. In another embodiment, the additional polymer is albumin. In another embodiment, the nanoshell comprises a polysaccharide. In another embodiment, the nanoshell comprises a saccharide.

In another embodiment, the present invention further provides that a nanocapsule encapsulates an inner liquid core, a solid core, or a partly liquid and partly solid core. In another embodiment, the present invention further provides that a nanocapsule or a nanoparticle of the invention has a diameter of 10 nm-100 nm. In another embodiment, the present invention further provides that a nanocapsule or a nanoparticle of the invention has a diameter of 5 nm-80 nm. In another embodiment, the present invention further provides that a nanocapsule or a nanoparticle of the invention has a diameter of 10 nm-70 nm. In another embodiment, the present invention further provides that a nanocapsule or a nanoparticle of the invention has a diameter of 20 nm-60 nm. In another embodiment, the present invention further provides that a nanocapsule or a nanoparticle of the invention has a structure comprising a nano-vesicular system that is formed in a core-shell arrangement.

In another embodiment, the present invention further provides that a core is devoid of a surfactant or is substantially free of a surfactant. In another embodiment, the present invention further provides that the nanocapsule and nanoparticle of the invention has low solubility within the water-soluble protein (polymer) particle to ensure that the active substance such as a sparingly water soluble substance is carried throughout the system properly and is released at the proper time and location. In another embodiment, the nanocapsule and nanoparticle of the invention is present within an emulsion that is uniformly dispersed in water.

In another embodiment, the present invention further provides that the free bioactive compound has maximal aqueous solubility below 5 g/l (water). In another embodiment, the present invention further provides that the free bioactive compound has maximal aqueous solubility below 3 g/l (water). In another embodiment, the present invention further provides that the free bioactive compound has maximal aqueous solubility below 2 g/l (water). In another embodiment, the present invention further provides that the free bioactive compound has maximal aqueous solubility below 1.5 g/l (water). In another embodiment, the present invention further provides that the free bioactive compound has maximal aqueous solubility below 0.5 g/l (water). In another embodiment, the present invention further provides that the free bioactive compound has maximal aqueous solubility below 0.1 g/l (water).

In another embodiment, the present invention further provides that the bioactive compound is an amino-acid or a peptide. In another embodiment, the present invention further provides that the bioactive compound is a non-polar amino-acid or a peptide. In another embodiment, the present invention further provides that the bioactive compound is a vitamin. In another embodiment, the present invention further provides that the bioactive compound is an oil-soluble vitamin. In another embodiment, the present invention further provides that the bioactive compound is a polyunsaturated fatty acid. In another embodiment, the present invention further provides that the bioactive compound is an antioxidant. In another embodiment, the present invention further provides that the bioactive compound is phytochemical. In another embodiment, the present invention further provides that the bioactive compound is an ester of any aforementioned compound described herein. In another embodiment, the bioactive compound is a lipid. In another embodiment, the bioactive compound is a phospholipid. In another embodiment, the bioactive compound is a glycolipid. In another embodiment, the bioactive compound is a nutraceutical. In another embodiment, the bioactive compound is a drug. In another embodiment, the bioactive compound is a combination of compounds.

In another embodiment, the concentration ratio of lipid to potato protein is 20:1 to 1:20. In another embodiment, the concentration ratio of lipid to potato protein is 5:1 to 1:10. In another embodiment, the concentration ratio of lipid to potato protein is 1:1 to 1:10. In another embodiment, the concentration ratio of lipid to potato protein is 1:5 to 1:40. In another embodiment, the concentration ratio of lipid to potato protein is 1:5 to 1:25. In another embodiment, the concentration ratio of lipid to potato protein is 1:5 to 1:15.

In another embodiment, the bioactive compound is an Omega-3 fatty acid. In another embodiment, the bioactive compound is an Omega-6 fatty acid. In another embodiment, the bioactive compound is an Omega-9 fatty acid. In another embodiment, the bioactive compound is an essential fatty acid. In another embodiment, the bioactive compound is an oil such as but not limited to flax seed oil. In another embodiment, the bioactive compound is Linoleic Acid (LA). In another embodiment, the bioactive compound is Linolenic Acid (LNA). In another embodiment, the bioactive compound comprises LA, LNA, or both. In another embodiment, the bioactive compound is a sterol. In another embodiment, the bioactive compound is a phytosterol. In another embodiment, the bioactive compound is a zoosterol. In another embodiment, the bioactive compound is vitamin D.

In another embodiment, the bioactive compound is vitamin A. In another embodiment, the bioactive compound is vitamin E. In another embodiment, the bioactive compound is vitamin K. In another embodiment, the bioactive compound is docosahexaenoic acid (DHA) or an ester thereof. In another embodiment, the bioactive compound is alpha lipoic acid. In another embodiment, the bioactive compound is a carotenoid. In another embodiment, the bioactive compound is beta-Carotene. In another embodiment, the bioactive compound is lutein.

In another embodiment, the diameter of the nanoparticle or the nanocapsule is 5 to 200 nm. In another embodiment, the diameter of the nanoparticle or the nanocapsule is 10 to 100 nm. In another embodiment, the diameter of the nanoparticle or the nanocapsule is 10 to 80 nm. In another embodiment, the diameter of the nanoparticle or the nanocapsule is 10 to 50 nm. In another embodiment, the diameter of the nanoparticle or the nanocapsule is 30 to 100 nm. In another embodiment, the diameter of the nanoparticle or the nanocapsule is 60 to 100 nm.

In another embodiment, a potato protein is from a source of potato protein isolate. In another embodiment, a potato protein is from a source of potato protein isolate having over 80% crude protein weight per dry weight. In another embodiment, a potato protein is from a source of potato protein isolate having over 85% crude protein weight per dry weight. In another embodiment, a potato protein is from a source of potato protein isolate having over 90% crude protein weight per dry weight. In another embodiment, a potato protein is from a source of potato protein isolate having over 95% crude protein weight per dry weight. In another embodiment, a potato protein is a potato protein isolate having over 97% crude protein weight per dry weight.

In another embodiment, a potato protein is a fraction of a potato protein. In another embodiment, a potato protein is patatin. In another embodiment, a potato protein is a protease inhibitor. In another embodiment, a potato protein is a phosphorylase. In another embodiment, a potato protein is a native potato protein. In another embodiment, a potato protein is a potato protein or a fraction thereof in pure form. In another embodiment, a potato protein, fractions of potato proteins and methods for obtaining the same are described in U.S. Pat. No. 8,465,911 which is hereby incorporated by reference in its entirety.

In another embodiment, the present invention further provides a composition comprising the nanocapsules or the nanoparticles in an aqueous solution. In another embodiment, the present invention further provides that the composition comprising the nanocapsules or the nanoparticles is a nanoemulsion. In another embodiment, the present invention further provides that the aqueous solution is a transparent aqueous liquid. In another embodiment, the present invention further provides that the aqueous solution is a beverage. In another embodiment, the present invention further provides that the aqueous solution is devoid of an additional emulsifier.

In another embodiment, the aqueous solution is transparent. In another embodiment, the aqueous solution comprises at least 70% by weight water. In another embodiment, the aqueous solution comprises at least 75% by weight water. In another embodiment, the aqueous solution comprises at least 85% by weight water. In another embodiment, the aqueous solution comprises at least 90% by weight water. In another embodiment, the aqueous solution comprises at least 95% by weight water. In another embodiment, the aqueous solution comprises at least 98% by weight water.

In another embodiment, the present invention further provides that the composition of the invention is stable for at least 10 to 120 seconds at pH=2 to 4 and at temperature of 65 to 80° C. In another embodiment, the present invention further provides that the composition of the invention is stable for at least 10 to 90 seconds at pH=2 to 3 and at temperature of 70 to 80° C. In another embodiment, the present invention further provides that the composition of the invention is stable for up to 60 seconds at pH=2 to 4 and at temperature of 70 to 75° C. In another embodiment, the present invention further provides that the composition of the invention is stable for at least 60 seconds at pH=2.5 and at a temperature of 72° C.

In another embodiment, the present invention further provides that the composition of the invention is stable for at least 10 to 90 hours at pH=2-3 and at temperature of 15 to 35° C. In another embodiment, the present invention further provides that the composition of the invention is stable for up to 40 hours at pH 2 to 4 and at temperature of 20 to 30° C. In another embodiment, the present invention further provides that the composition of the invention is stable for at least 24 to 36 hours at pH=2.5 and at temperature of 23 to 27° C. In another embodiment, the present invention further provides that the composition of the invention is stable for at least 24 hours at pH=2.5 and a temperature of 25° C. In another embodiment, the present invention further provides that the composition of the invention is stable for up to 24 hours at pH=2.5 and a temperature of 25° C.

In another embodiment, the phrase: "the potato protein and the bioactive compound" is synonymous with the phrase "the potato protein bound to the bioactive compound".

In another embodiment, the present invention further provides that the potato protein is insoluble at a neutral pH. In another embodiment, the present invention further provides that the potato protein is insoluble at a basic pH. In another embodiment, the present invention further provides that the potato protein is soluble at an acidic pH.

In another embodiment, the present invention further provides that the potato protein and the bioactive compound are insoluble at a neutral pH. In another embodiment, the present invention further provides that the potato protein and the bioactive compound are insoluble at a basic pH. In another embodiment, the present invention further provides that the potato protein and the bioactive compound are soluble at an acidic pH.

In another embodiment, the present invention further provides that freeze-drying the potato protein renders the potato protein soluble at a neutral pH.

In another embodiment, the present invention further provides that freeze-drying the potato protein and the bioactive compound renders the potato protein and the bioactive compound soluble at a neutral pH. In another embodiment, the present invention further provides that the process of making a composition of the invention comprises the steps of: (1) mixing the potato protein and the bioactive compound in an aqueous acidic solution; (2) freeze-drying the acidic solution comprising the potato protein and the bioactive compound, thus obtaining a freeze-dried composition of a potato protein and a bioactive compound; (2) re-suspending the freeze-dried composition of a potato protein and a bioactive compound in an aqueous solution having a neutral pH.

In another embodiment, neutral pH includes pH values from 6.5 to 7.5. In another embodiment, neutral pH includes pH values from 6.0 to 8.0. In another embodiment, acidic pH includes pH values from 6.9 to 1. In another embodiment, acidic pH includes pH values from 6.5 to 4. In another embodiment, basic pH includes pH values from 7.5 to 10.

In another embodiment, the present invention further provides that the bioactive compound is present at a concentration of 0.1 microgram/ml to 1 mg/ml. In another embodiment, the present invention further provides that the bioactive compound is present at a concentration of 1 microgram/ml to 1 mg/ml. In another embodiment, the present invention further provides that the bioactive compound is present at a concentration of 100 microgram/ml to 1 mg/ml. In another embodiment, the present invention further provides that the bioactive compound is present at a concentration of 100 microgram/ml to 0.5 mg/ml. In another embodiment, the present invention further provides that the bioactive compound is present at a concentration of 500 microgram/ml to 1 mg/ml. In another embodiment, the present invention further provides that the bioactive compound is present at a concentration of 0.1 mg/ml to 1 mg/ml. In another embodiment, the present invention further provides that the bioactive compound is present at a concentration of 0.5 mg/ml to 1 mg/ml. In another embodiment, the present invention further provides that the bioactive compound is present at a concentration of 0.5 mg/ml to 5 mg/ml.

In another embodiment, the present invention further provides that the nanoparticles and/or nanocapsules or any composition comprising the nanoparticles and/or nanocapsules is/are devoid of a surfactant. In another embodiment, the present invention further provides that the nanoparticles and/or nanocapsules or any composition comprising the nanoparticles and/or nanocapsules is/are devoid of a low molecular weight surfactant.

In another embodiment, a composition of the invention is devoid of an anionic polyelectrolyte. In another embodiment, a composition of the invention is devoid of an organic solvent. In another embodiment, a composition of the invention is devoid of an alcohol. In another embodiment, a composition of the invention in the form of a solution is free of an emulsifier. In another embodiment, a composition of the invention comprises a water miscible solvent such as ethanol or DMSO in a trace amount.

In another embodiment, a composition of the invention comprises less than 5% in weight a water miscible solvent such as ethanol. In another embodiment, a composition of the invention comprises less than 2.5% in a water miscible solvent such as ethanol. In another embodiment, a composition of the invention comprises less than 1% in weight of a water miscible solvent such as ethanol. In another embodiment, a composition of the invention comprises less than 0.5% in weight a water miscible solvent such as ethanol. In another embodiment, a composition of the invention comprises less than 0.1% in weight a water miscible solvent such as ethanol.

In another embodiment, a composition of the invention is devoid of an alcohol. In another embodiment, nanoparticles and/or nanocapsules are formed and entrapped simultaneously in one stage. In another embodiment, the process of making the nanoparticles and/or nanocapsules of the invention is devoid of heating.

In another embodiment, the present invention further provides a method of supplementing a subject with a bioactive compound of the invention, comprising the step of administering to the subject a composition comprising: the aqueous liquid, a bioactive compound, and a potato protein, thereby supplementing a subject with a bioactive compound. In another embodiment, the aqueous liquid comprises a bioactive compound bound to the potato protein, thereby supplementing a subject with a bioactive compound. In another embodiment, an aqueous liquid is a transparent aqueous liquid comprising nanocapsules or nanoparticles of the invention.

In another embodiment, a subject is a human. In another embodiment, a subject is a pet. In another embodiment, a subject is a farm animal. In another embodiment, a subject is a rodent. In another embodiment, a subject is an infant. In another embodiment, a subject is a toddler.

In another embodiment, the present invention further provides a method of supplementing a subject with a nutraceutical as a bioactive compound, comprising the step of administering to the subject a composition comprising: an aqueous liquid, a nutraceutical as a bioactive compound, and a potato protein, thereby supplementing a subject with a nutraceutical as a bioactive compound. In another embodiment, the composition comprising a nutraceutical is administered orally. In another embodiment, the nutraceutical is any non-toxic food component which has demonstrated health benefits. In another embodiment, the nutraceutical is any sparingly water soluble, non-toxic food component, which has demonstrated health benefits.

In another embodiment, the nutraceutical is an omega-3 fatty acid such as α-linolenic acid (ALA) and/or eicosapentaenoic acid (EPA). In another embodiment, the nutraceutical is sea food PUFA such as EPA and docosahexaenoic acid (DHA). In another embodiment, the nutraceutical is DHASCO (DHA single cell oil). In another embodiment, the nutraceutical is a monounsaturated fatty acid (MUFAs) such as oleic acid. In another embodiment, the nutraceutical is medium-chain fatty acids (MCFAs) and/or medium-chain triacylglycerol (MCT). In another embodiment, the nutraceutical is conjugated linoleic acid (CLA) and/or γ-linolenic acid. In another embodiment, the nutraceutical is diacylglycerol (DAG) oil. In another embodiment, the nutraceutical is a triacyl glycerol (TAG). In another embodiment, the nutraceutical is a phospholipid.

In another embodiment, the present invention further provides a method of supplementing a subject with a bioactive compound of the invention, comprising the step of administering to the subject a nano-emulsion composition comprising: an aqueous liquid, a bioactive compound, and a potato protein, thereby supplementing a subject with a bioactive compound.

In another embodiment, the subject is afflicted with a disease requiring essential fatty acids support. In another embodiment, the subject is afflicted with a cardiovascular disease. In another embodiment, the subject is afflicted with a reproductive disease. In another embodiment, the subject is afflicted with an immune disease. In another embodiment, the subject is afflicted with a nervous system disease.

In another embodiment, the subject is an infant and the composition is used for supplementing required essential fatty acids for neural development and maturation of sensory systems. In another embodiment, the composition is used for supplementing required essential fatty acids/lipids for treating health conditions such as but not limited to: skin diseases and pathologies, hair loss, behavioral changes, failure to heal wounds, miscarriages, arthritic conditions, increased cholesterol, growth retardation, depression, dyslexia, impaired vision, learning problems in children, heart attacks, cancer, insulin resistance, asthma, lupus, schizophrenia, accelerated aging, stroke, obesity, diabetes, ADHD, and alzheimer's disease, etc.

In another embodiment, the bioactive compound is an eicosanoid, an arachidonic acid, or any derivative thereof. In another embodiment, a bioactive compound of the invention such as prostaglandin E 2 (PGE 2) is used to suppress the immune response of a subject. In another embodiment, a bioactive compound of the invention such as PGE2 is used to promote cell growth of a subject. In another embodiment, a bioactive compound of the invention such as PGE2 is used as a vasodilator. In another embodiment, a bioactive compound of the invention such as PGE2 is used to induce and/or enhance the formation of anti-inflammatory lipoxins in a subject.

In another embodiment, a bioactive compound of the invention such as Prostaglandin I(2) (PGI(2)) is used to suppress the immune response of a subject. In another embodiment, a bioactive compound of the invention such as PGI(2) is used to inhibit platelet aggregation in a subject. In another embodiment, a bioactive compound of the invention such as PGI(2) is used as a potent vasodilator.

In another embodiment, a bioactive compound of the invention such as Thromboxane A2 (TXA2) is used to suppress the immune response of a subject. In another embodiment, a bioactive compound of the invention such as TXA2 is used as a vasoconstrictor.

In another embodiment, a bioactive compound of the invention such as Prostaglandin D2 (PGD2) is used to inhibit platelet aggregation in a subject. In another embodiment, a bioactive compound of the invention such as PGD2 is used as a sleep promoter in a subject. In another embodiment, a bioactive compound of the invention such as PGD2 is used as a vasodilator.

In another embodiment, a bioactive compound of the invention such as 12-hydroxy-5,8,10,14-eicosatetraenoic acid (12-HETE) is used as a neutrophil chemo-attractant. In another embodiment, a bioactive compound of the invention such as 12-HETE is used as a stimulator of glucose-induced insulin secretion. In another embodiment, a bioactive compound of the invention such as 15-Hydroxyeicosatetraenoic acid (15-HETE) is used as an inhibitor of 5- and 12-lipoxygenase. In another embodiment, a bioactive compound of the invention such as Lipoxin A is used as a chemoattractant. In another embodiment, a bioactive compound of the invention such as Lipoxin B is used as an inhibitor of NK cell activity.

In another embodiment, a bioactive compound of the invention such as a fatty acid is used, for example, in the treatment of chronic diseases such as but not limited to: CHD, obesity, diabetes, and specific types of cancers as are known to one of average skill in the art. In another embodiment, a bioactive compound of the invention is used, for example, in the treatment of vitamin D deficiency.

In another embodiment, the invention further provides a kit comprising the nanoparticles or nanocapsules of the invention in liquid or dry form and dosing, mixing, and/or formulating instructions. In another embodiment, the invention further provides a kit comprising the nanoparticles or nanocapsules of the invention and dosing, mixing, and/or formulating instructions with an aqueous solution as described herein. In another embodiment, the invention further provides a kit comprising the nanoparticles or nanocapsules, an aqueous solution as described herein and dosing, mixing, and/or formulating instructions.

In one embodiment, compositions of the present invention are presented in a pack or dispenser device, such as an FDA approved kit, which contain one or more unit dosage forms containing the nanoparticles or nanocapsules. In one embodiment, the pack, for example, comprise metal or plastic foil, such as a blister pack. In one embodiment, the pack or dispenser device is accompanied by instructions for administration. In one embodiment, the pack or dispenser is accommodated by a notice associated with the container in a form prescribed by a governmental agency regulating the manufacture, use or sale of pharmaceuticals and/or nutraceuticals, which notice is reflective of approval by the agency of the form of the compositions or human or veterinary administration. Such notice, in one embodiment, is labeling approved by the U.S. Food and Drug Administration for prescription drugs or of an approved product insert.

In some embodiments, preparation of effective amount or dose can be estimated initially from in vitro assays. In one embodiment, a dose can be formulated in animal models and such information can be used to more accurately determine useful doses in humans.

In one embodiment, toxicity and therapeutic efficacy of the nanoparticles or nanocapsules described herein can be determined by standard pharmaceutical procedures in vitro, in cell cultures or experimental animals. In one embodiment, the data obtained from these in vitro and cell culture assays and animal studies can be used in formulating a range of dosage for use in human. In one embodiment, the dosages vary depending upon the dosage form employed and the route of administration utilized. In one embodiment, the exact formulation, route of administration and dosage can be chosen by the individual physician in view of the patient's condition. [See e.g., Fingl, et al., (1975) "The Pharmacological Basis of Therapeutics", Ch. 1 p. 1].

In one embodiment, depending on the severity and responsiveness of the condition to be treated, dosing can be of a single or a plurality of administrations, with course of treatment lasting from several days to several weeks or until cure is effected or diminution of the disease state is achieved.

In one embodiment, the amount of a composition to be administered will, of course, be dependent on the subject being treated, the severity of the affliction, the manner of administration, the judgment of the prescribing physician, etc.

In one embodiment, the nanocapsules and/or nanoparticles of the present invention can be provided to the individual per se (as a powder for example). In one embodiment, the nanocapsules and/or nanoparticles of the present invention can be provided to the individual as part of a pharmaceutical composition where it is mixed with a pharmaceutically acceptable carrier.

In one embodiment, a "pharmaceutical composition" refers to a preparation of one or more nanocapsules and/or nanoparticles described herein with other chemical components such as physiologically suitable carriers and excipients. The purpose of a pharmaceutical composition is to facilitate administration of nanocapsules and/or nanoparticles to an organism.

In one embodiment, the phrases "physiologically acceptable carrier" and "pharmaceutically acceptable carrier" which are interchangeably used refer to a carrier or a diluent that does not cause significant irritation to an organism and does not abrogate the biological activity and properties of the administered compound. An adjuvant is included under these phrases. In one embodiment, one of the ingredients included in the pharmaceutically acceptable carrier can be for example polyethylene glycol (PEG), a biocompatible polymer with a wide range of solubility in both organic and aqueous media (Mutter et al. (1979).

In one embodiment, "excipient" refers to an inert substance added to a pharmaceutical composition to further facilitate administration of nanocapsules and/or nanoparticles. In one embodiment, excipients include calcium carbonate, calcium phosphate, various sugars and types of starch, cellulose derivatives, gelatin, vegetable oils and polyethylene glycols.

Techniques for formulation and administration of drugs are found in "Remington's Pharmaceutical Sciences," Mack Publishing Co., Easton, Pa., latest edition, which is incorporated herein by reference.

In one embodiment, suitable routes of administration, for example, include oral, rectal, transmucosal, transnasal, intestinal or parenteral delivery, including intramuscular, subcutaneous and intramedullary injections as well as intrathecal, direct intraventricular, intravenous, intraperitoneal, intranasal, or intraocular injections.

In one embodiment, the preparation is administered in a local rather than systemic manner, for example, via injection of the preparation directly into a specific region of a patient's body.

Oral administration, in one embodiment, comprises a unit dosage form comprising solutions, suspensions, emulsions and the like. Such unit dosage forms comprise a safe and effective amount of the desired nanocapsules and/or nanoparticles.

Peroral compositions, in some embodiments, comprise liquid solutions, emulsions, suspensions, and the like.

In some embodiments, compositions for use in the methods of this invention comprise solutions or emulsions, which in some embodiments are aqueous solutions or emulsions comprising a safe and effective amount of the nanocapsules and/or nanoparticles of the present invention and optionally, other compounds. In some embodiments, the compositions comprise from about 0.01% to about 10.0% w/v of a subject compound, more preferably from about 0.1% to about 2.0.

Further, in another embodiment, the pharmaceutical compositions are administered topically to body surfaces, and are thus formulated in a form suitable for topical administration. Suitable topical formulations include gels, ointments, creams, lotions, drops and the like. For topical administration, the nanocapsules and/or nanoparticles of the present invention are combined with an additional appropriate therapeutic agent or agents, prepared and applied as solutions, suspensions, or emulsions in a physiologically acceptable diluent with or without a pharmaceutical carrier.

In one embodiment, pharmaceutical compositions of the present invention are manufactured by processes well known in the art, e.g., by means of conventional mixing, dissolving, granulating, dragee-making, levigating, emulsifying, encapsulating, entrapping or lyophilizing processes.

In one embodiment, injectables, of the invention are formulated in aqueous solutions. In one embodiment, injectables, of the invention are formulated in physiologically compatible buffers such as Hank's solution, Ringer's solution, or physiological salt buffer. In some embodiments, for transmucosal administration, penetrants appropriate to the barrier to be permeated are used in the formulation. Such penetrants are generally known in the art.

In one embodiment, the preparations described herein are formulated for parenteral administration, e.g., by bolus injection or continuous infusion. In some embodiments, formulations for injection are presented in unit dosage form, e.g., in ampoules or in multidose containers with optionally, an added preservative. In some embodiments, compositions are suspensions, solutions or emulsions in aqueous vehicles, and contain formulatory agents such as suspending, stabilizing and/or dispersing agents.

The compositions also comprise, in some embodiments, preservatives, such as benzalkonium chloride and thimerosal and the like; chelating agents, such as edetate sodium and others; buffers such as phosphate, citrate and acetate; tonicity agents such as sodium chloride, potassium chloride, glycerin, mannitol and others; antioxidants such as ascorbic acid, acetylcystine, sodium metabisulfote and others; aromatic agents; viscosity adjustors, such as polymers, including cellulose and derivatives thereof; and polyvinyl alcohol and acid and bases to adjust the pH of these aqueous compositions as needed. The compositions also comprise, in some embodiments, local anesthetics or other actives. The compositions can be used as sprays, mists, drops, and the like.

In another embodiment, the pharmaceutical composition is delivered in a controlled release system is formulated for intravenous infusion, implantable osmotic pump, transdermal patch, or other modes of administration. In one embodiment, a pump is used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989). Other controlled release systems are discussed in the review by Langer (Science 249:1527-1533 (1990).

In some embodiments, the nanocapsules and/or nanoparticles are in powder form and possibly in kits for constitution with a suitable vehicle, e.g., sterile, pyrogen-free water based solution or a beverage, before use. Compositions are formulated, in some embodiments, for atomization and inhalation administration. In another embodiment, compositions are contained in a container with attached atomizing means.

In one embodiment, the preparation of the present invention is formulated in rectal compositions such as suppositories or retention enemas, using, e.g., conventional suppository bases such as cocoa butter or other glycerides.

In one embodiment, nanocapsules or nanoparticles of the invention are made by a process comprising the steps of: preparing solution 1 comprising: (a) dissolving the potato protein in water at a concentration of 0.1-100 g/L and typically at a concentration of 0.7 to 1.5 g/L; (b) stirring/mixing the solution for 20 minutes to 20 hours and typically for 0.5 to 2 hours at 4 to 40° C. and typically at 25° C.; (c) after complete dissolution the solution is filtered through a filter having a cutoff of 0.1 to 2 micron; preparing solution 2 comprising: (a) dissolving the bioactive compound in a water-miscible organic food grade solvent (typically absolute ethanol); combining solution 1 and solution 2 by drop-wise or slowly adding solution 2 into solution 1 and vigorous stirring. In another embodiment, vigorous stirring is performed by utilizing vortex.

In another embodiment, the final concentration of the organic solvent in the obtained aqueous solution is 0.001 to 20% and more typically 0.1 to 2%. In another embodiment, the final concentration of the organic solvent in the obtained aqueous solution is 0.01 to 10%. In another embodiment, the final concentration of the organic solvent in the obtained aqueous solution is 0.01 to 1%. In another embodiment, the final concentration of the organic solvent in the obtained aqueous solution is 0.1 to 5%. In another embodiment, the final concentration of the organic solvent in the obtained aqueous solution is 0.1 to 5%. In another embodiment, the final concentration of the organic solvent in the obtained aqueous solution is 0.1 to 1%.

In another embodiment, the combined solution 1 and solution 2 is further filtered through a filter having cutoff of 0.1 to 15 micron. In another embodiment, the filter of the invention has a cutoff of 0.2 to 5 micron. In another embodiment, the filter of the invention has a cutoff of 0.1 to 0.8 micron. In another embodiment, the filter of the invention has a cutoff of 0.2 to 0.5 micron. In another embodiment, the filter of the invention has a cutoff of 0.1 to 0.45 micron.

In another embodiment, the combined mix of solution 1 and solution 2, filtered or unfiltered, is further dried according to methods known in the art and a powder is obtained. In another embodiment, the combined mix of solution 1 and solution 2, filtered or unfiltered, is freeze dried. In another embodiment, a cryoprotectant (e.g. trehalose or maltodextrin) is further utilized. In another embodiment, the combined mix of solution 1 and solution 2, filtered or unfiltered, is quench frozen (e.g. by liquid nitrogen). In another embodiment, a powder comprising or consisting the resulting nanocapsules or nanoparticles of the invention is obtained. In another embodiment, a powder comprising or consisting the resulting nanocapsules or nanoparticles of the invention is reconstituted by adding a known amount of the powder to an aqueous solution, while stirring, thereby obtaining a composition of the invention.

EXAMPLES

Example 1

Potato Protein Nanoencapsulated Products

The present example provides scientific evidences pertinent to the freezing, drying, dry-state stability, and reconstitutability of the nanoencapsulated compositions of the invention including real beverage products.

This example provides evidence showing that the current technology enables the enrichment of soft drinks with health promoting nutraceuticals. Those drinks treated according to the present technology provided, long desired, preventive medicine benefits. Needless to say, the encapsulation of bioactives by this technology should be applied in many other food and drink products, where solubilization and protection of sparingly soluble bioactive compounds are desired.

First, the effect of potato protein on solubilization and transparency of vitamin D (VD) was assessed. Two aqueous buffer solutions (25 mM phosphate buffer, pH 2.5) containing the same concentration of VD (0.1 mg/ml) were used. Only one vial (left vial of FIG. 1a) also included 1.5 mg/ml potato protein. It is clearly seen that due to the presence of the potato protein, the solution containing VD is transparent, while the one devoid of potato protein is turbid.

Second, the effect of potato protein on solubilization and transparency of omega 3 was also assessed. Specifically, two aqueous buffer solutions (25 mM phosphate buffer, pH 2.5) contained the same concentration of 0.5 ul/ml omega 3 (ethyl ester DHA) colored with Nile red, which is only pink in a hydrophobic environment. One vial (left vial of FIG. 1b) also contained 1.5 mg/ml potato protein.

The results provided in FIG. 1 clearly demonstrate that in the absence of potato protein the solutions of VD and omega 3 are much more turbid then in the presence of the protein. Thus, the potato protein nanoparticle solubilized the hydrophobic ingredient in a uniform, transparent, manner.

VD—Potato Protein Interactions

Figure 4:
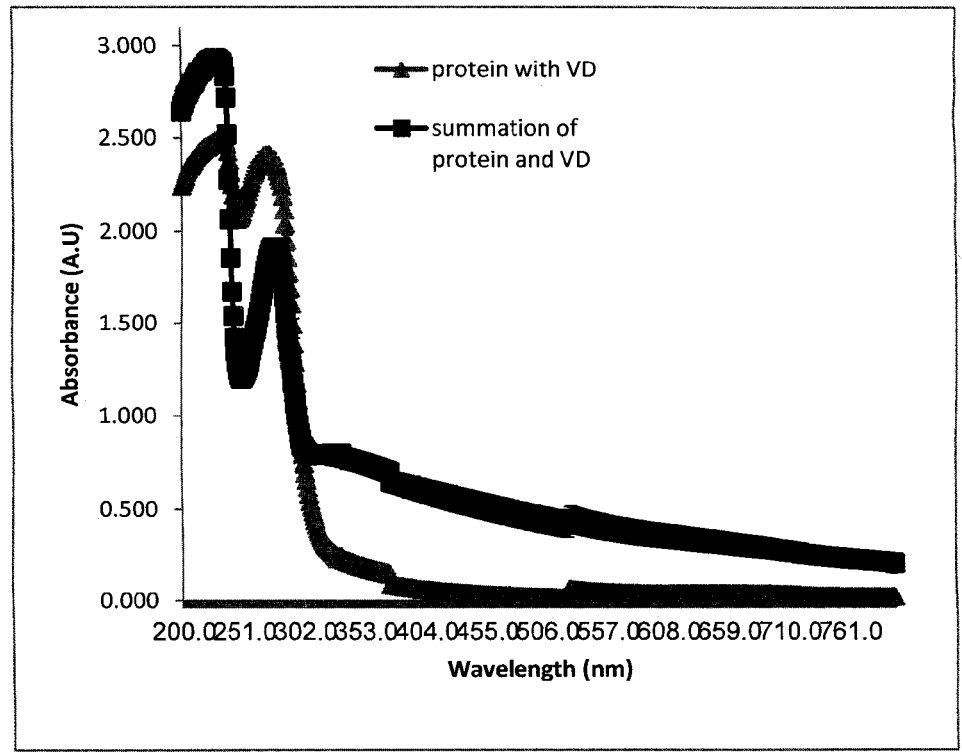
FIG. 4. UV absorbance spectra of VD and potato protein complex (light gray) and the summation of the spectra of VD alone and of potato protein alone (dark grey).

FIG. 4, clearly demonstrates that the VD absorbance spectrum in potato protein complexes is different from the respective mathematical summation of the two individual spectra. These results provide evidence that there are molecular interactions between VD and the potato protein.

Particle Size Distribution

Dynamic light scattering (DLS) was used to evaluate size distribution of the potato protein-VD complexes.

The particle size of VD without potato protein was measured with different concentration of VD—10, 25, 35 and 50 ug/ml VD in a phosphate buffer (25 mM, pH 2.5). In all concentrations a bimodal distribution was obtained, with diameter larger than 1500 nm.

Figure 3:
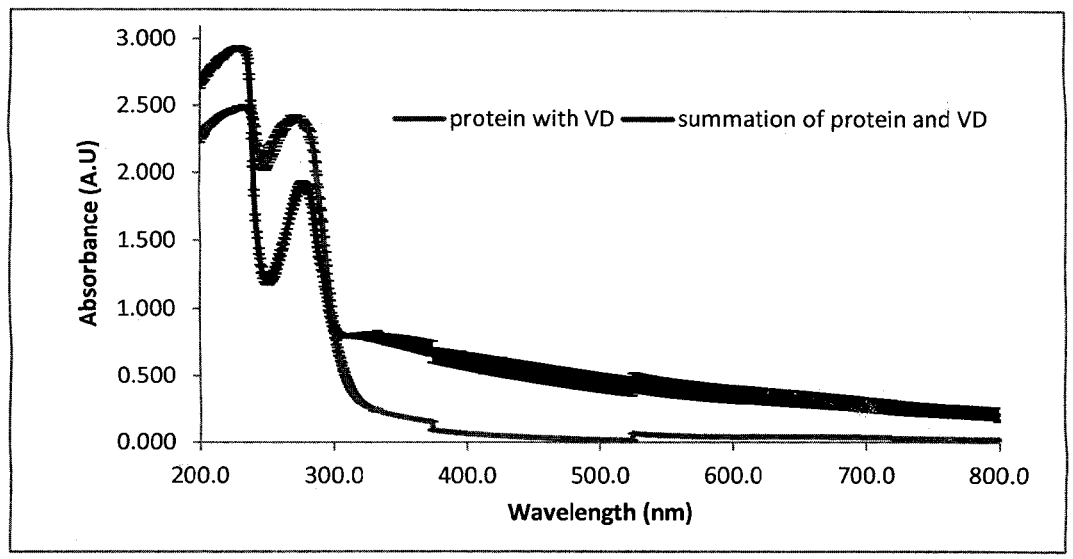
FIG. 3. A graph showing a particle size distribution of a solution containing 1 mg/ml potato protein isolate, and 25 μg/ml $VD_3$ in phosphate buffer (25 mM, pH 2.5). Under these conditions the particle size of $VD_3$ in a protein-free solution was >1500 nm.

The size distributions of the VD—potato protein nanoparticles were also measured at several concentrations of VD—10, 25, 35 and 50 μg/ml VD. The size distributions (FIG. 3) consisted of two fractions. The first fraction (84% by volume) comprised the small nano-particles of about 15 nm diameter, while the second fraction comprised nanoparticles whose average diameter was around 80 nm.

Stability

Figure 5:
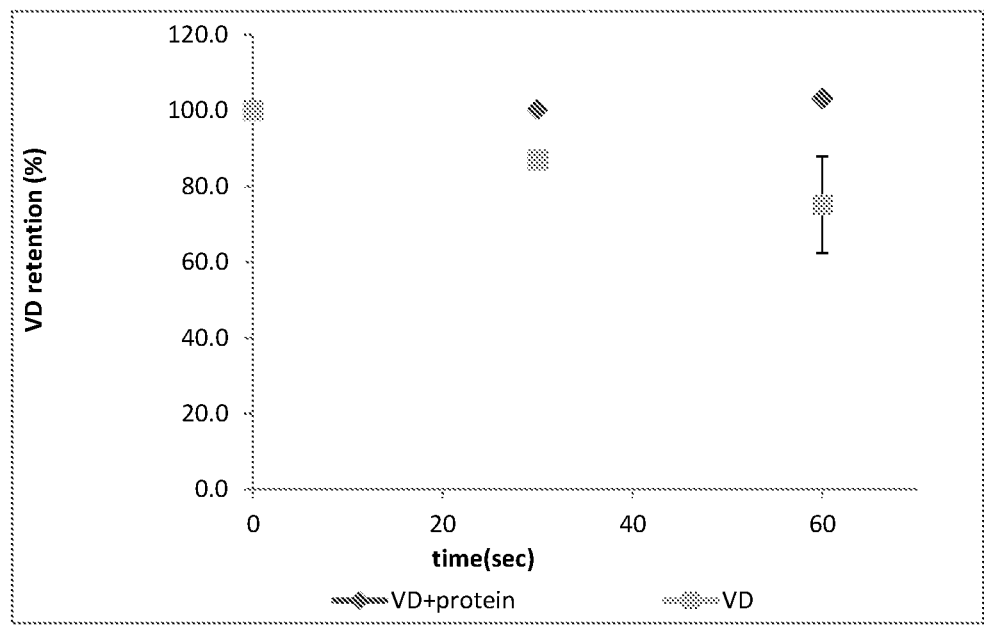
FIG. 5. A graph showing the percentage of VD retention within the composition during pasteurization at 72° C. and pH 2.5 for up to 60 seconds, in the presence and absence of 1.5 mg/ml potato protein (The error bars represent standard error of duplicates. When not seen, they are smaller than the symbols).

The percentage of VD retention within the composition was assessed during pasteurization at 72° C. and pH 2.5 for up to 60 seconds, in the presence and absence of 1.5 mg/ml potato protein. VD concentration at time zero was 0.1 mg/ml. The measurements were done using RP-HPLC. The samples were kept in the dark and the vials' head spaces were filled with argon to prevent oxidation until the analysis. As seen in FIG. 5, the potato protein conferred significant protection to VD against heat induced degradation at 72° C. and pH 2.5 for at least 60 seconds.

Figure 6:
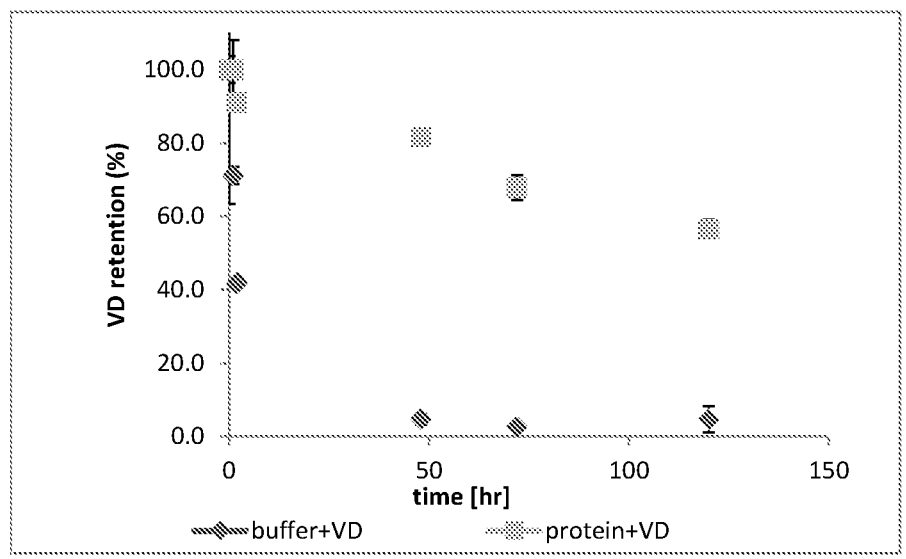
FIG. 6. Is a graph showing the percentage of VD retention within the composition at pH 2.5, and 25° C., in the presence (diamonds) and absence (squares) of 1.5 mg/ml potato protein. VD concentration at time zero was 0.1 mg/ml. The measurements were done using RP-HPLC (The error bars represent standard error of duplicates. When not seen, they are smaller than the symbols).

The percentage of VD retention within the composition at pH 2.5, and 25° C. was also assessed, in the presence and absence of 1.5 mg/ml potato protein. VD concentration at time zero was 0.1 mg/ml. As shown in FIG. 6 the potato protein conferred significant protection to VD under these conditions. The measurements were done using RP-HPLC. Similar results are obtained with omega 3 at both pH ranges.

The size of the nanoparticles, in all examples was 20-80 nm in diameter, which enables a clear solution, without the need for emulsifiers or of high pressure homogenization procedures.

Example 2

Stability of Potato Protein (PP) Nanoencapsulated Products

Determination of VD3 Degradation Under Typical Industrial Pasteurization and Hot-Bottling Conditions VD3 in phosphate buffer, and PP-VD3 nanoparticles were prepared at 1 mg/ml potato protein (PP) and 100 µg/ml VD3 at pH 2.5.

Samples (without a cap) were heated in a water bath for 1 min at 88° C. Following heat treatment, samples were capped and maintained at room temperature for 30 minutes until their temperature decreased to 30-35° C. Controls of VD3, PP and PP-VD3 nanoparticles, at pH 2.5, were extracted immediately without any heat treatment. The other samples were extracted at room temp after the above heat treatment.

VD3 Extraction

VD3 was extracted and quantified using a protocol based on Haham, et al. (Haham, M., et al., Stability and bioavailability of vitamin D nanoencapsulated in casein micelles. Food & Function, 2012). The protocol, used on both aqueous solutions (with and without PP), was as follows: 1 ml of VD3-containing sample was put into a glass test tube. 3 ml of a 2:1 chloroform:methanol mixture was then added, and the tubes were vortexed for ~20 seconds. Additional 2 ml of chloroform was added, and the tubes were vortexed for 1 minute. The tubes were then centrifuged for 10 minutes at 1,500 rca (×g) and 4° C., which caused the phases to separate into an upper, ~2 ml aqueous phase and a lower, ~4 ml organic phase containing the VD3. Using a glass syringe, 3 ml of the organic phase was transferred to a glass vial and dried under $N_2$ gas at 0.1 bar.

VD3 Quantification Via Reverse-Phase High-Performance Liquid Chromatography (RP-HPLC)

Following extraction, 1.5 ml of RP-HPLC mobile phase (methanol:acetonitrile:water 49.5:49.5:1, by volume) were added to the drying vial, given 15 minutes to equilibrate after vortexing, and then transferred to a 1.5 ml glass HPLC vial. Samples were run on an HP Agilent 1100 HPLC system equipped with a diode array detector (DAD), and a 4.8×250 mm Vytec™ C-18 column. 20 µl samples were isocratically eluted at a flow rate of 1.3 ml/min. Data analysis was conducted using the ChemStation software package (Hewlett-Packard, Wilmington, Del.). In the mobile phase, $VD_3$ has a local UV absorption maximum at 267 nm, and so the 267 nm chromatogram was used for $VD_3$ quantification.

At a flow rate of 1.3 ml/min, the peak eluted at a retention time of approximately 7 minutes. This peak was confirmed as $VD_3$ by observing its UV absorption spectrum, as recorded by the DAD. Moreover, by recording absorptions at both 228 nm and at 254 nm, the method provided an additional confirmation of vitamin D presence: peak area at 228 nm is ~0.7 of the peak area at 254 nm. This absorptivity ratio was consistent with the spectrum of vitamin D.

Shelf Life

PP-VD3 nanoparticles and VD3 suspensions were prepared in glass test tubes at pH 2.5, pasteurized for 1 min at 88° C. in open test tubes, and then capped, cooled and maintained at room temperature (23° C.) exposed to light, and followed with time. Samples for all shelf life tests were prepared without any preservative.

Samples of 1 ml containing 100 µg/ml VD3 in buffer and 1 mg/ml PP were prepared. The samples were individually prepared in order to perform total volume extractions, minimizing transfer/precipitation losses. Three tubes of each type were quantified immediately, to serve as control. All the remaining tubes were then pasteurized. Three tubes of each type were quantified immediately, to serve as reference. The other tubes were stored at the conditions described above. At each time point, three tubes of each type were taken from storage and their VD3 content was quantified. In all experiments, the tubes were stored covered with their lids to prevent evaporation.

Freeze Drying and Reconstitution of PP-VD3 Nanoparticles

The nanoparticles were prepared similarly to the method described above with slight modifications: 0.5 ml samples of VD-PP nanoparticles were prepared in Eppendorfs (1.5 ml total volume) as described above, with a final VD3 concentration of 200 µg/ml and a PP concentration of 2 mg/ml, pH 2.5. 50 mg maltodextrin were added to each Eppendorf, as a cryoprotective agent. After all samples were prepared the solutions were frozen by liquid nitrogen and freeze-dried. Three Eppendorfs were set aside before freezing, and quantified immediately, to serve as control. For reconstitution after freezing, 1 ml phosphate buffer was added to an Eppendorf, and the sample was vortexed.

The Eppendorfs were stored in a desiccator at room temperature. To examine the particle size of the reconstituted samples, DLS was used as described. For shelf life test, at different time points three Eppendorf underwent reconstitution and quantification of their vitamin content by HPLC.

Figure 7:
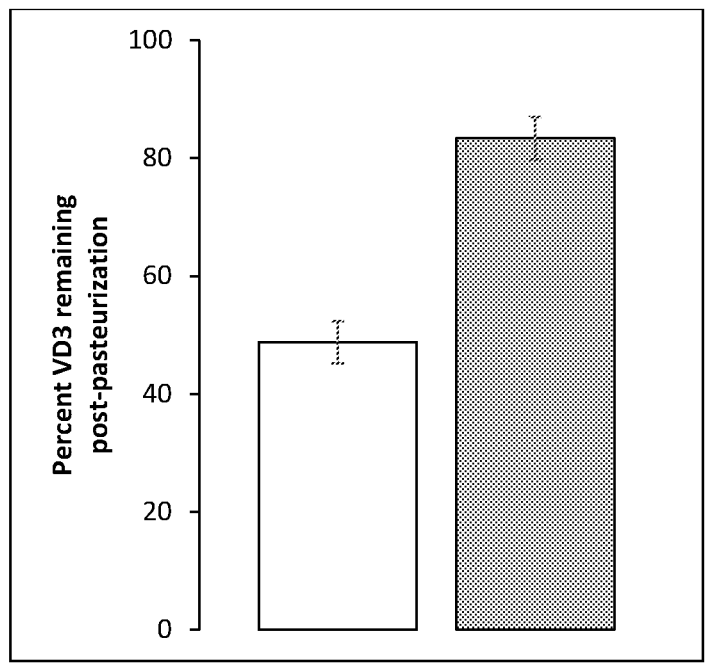
FIG. 7. Is a graph showing the percent of remaining VD3 in solutions initially containing 100 ug/ml VD3 with and without 1 mg/ml PP in 25 mM phosphate buffers, pH 2.5. The solutions were pasteurized at 88° C. for 1 min and cooled for 30 minutes until their temperature was 30-35° C. White: VD3, Gray: VD3-PP.

Determination of VD3 Degradation Under Typical Industrial Pasteurization and Hot-Bottling Conditions with and without Encapsulation with PP The protective role of PP over VD was studied during a typical thermal treatment and bottling of shelf-stable low pH beverages. FIG. 7 presents the results of the thermal degradation test. These results indicate that the heat treatment caused 55% of the unprotected VD to degrade, while only 16% of the VD complexed with PP were lost. This constituted a significant unexpected degree of protection conferred by the protein to VD, particularly at such a low pH where the vitamin is very sensitive.

Figure 8:
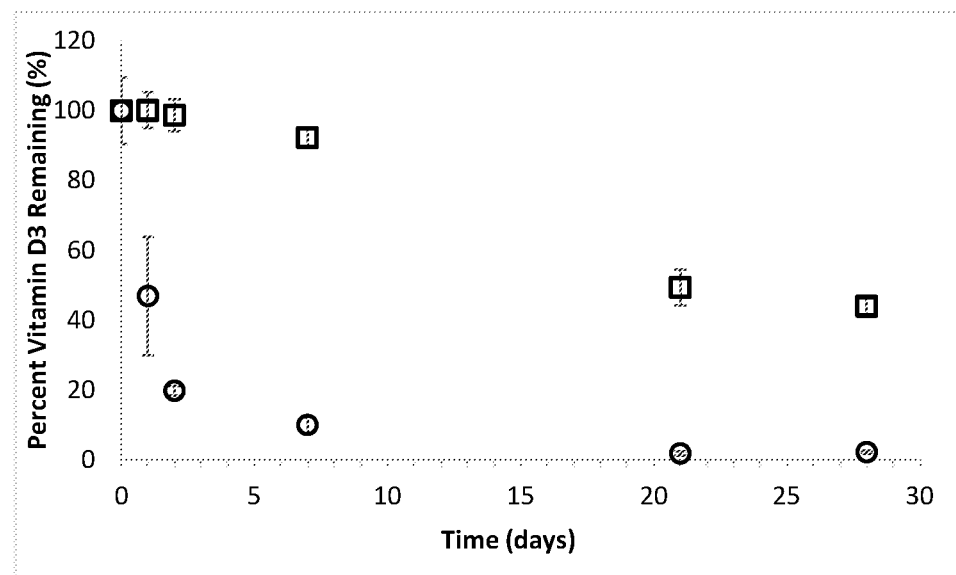
FIG. 8. Is a graph showing simulated shelf life test at 23° C. and pH 2.5. Circles: VD3 in phosphate buffer, squares: PP-VD3 complexes.

Further tests that show the great advantage of the present invention in conferring exceptional stability to active ingredient is provided in FIG. 8. FIG. 8 shows the percent VD3 remaining at each time point was calculated by comparing the VD content relatively to the VD content right after pasteurization. Thus, the shelf life test examined the VD3 stability at low pH (2.5) and exposure to light, during time.

In the absence of PP, most of the VD3 degraded within 24 hours; 52% of the post-pasteurization VD3 concentration was lost, and after a week almost all the VD was degraded. In contrast, the VD3-PP nanoparticles unexpectedly retained most of their VD3 content over one week period, losing only 8%. After 21 days at this low pH, to which VD is very sensitive, about 50% of the vitamin remained intact, and after 4 weeks, about 45% of the VD remained. It should be noted that dark storage conditions, and lower oxygen concentration existing e.g. in carbonated beverages would significantly improve VD retention.

Freeze Drying and Reconstitution of PP-VD3 Nanoparticles

To make the nanoparticles more applicable for the food industry, the usage of dried nanoparticles would serve as an advantage in terms of cost of transportation, length of shelf life and ease of formulation. Therefore the percentage of the vitamin which is lost during freeze drying was studied together with the reconstituted products in terms of transparency and nanoparticle size distribution using DLS.

The results obtained show that during the freeze drying and reconstitution most (80-96%) of the vitamin D in the PP-VD complexes survived. While adding the phosphate buffer to the powder, it was dissolved instantly and the solution obtained was completely clear and no aggregates were visible by eye. The DLS measurements show that three subpopulations of nanometer scale particles were obtained (Table 1).

TABLE 1 particle size of the reconstituted product

| Subpopulation | Average diameter (nm) | Standard error (nm) | Average volume fraction | Standard error |
|---|---|---|---|---|
| 1 | 13 | 1.1 | 0.90 | 0.009 |
| 2 | 74 | 15.9 | 0.06 | 0.005 |
| 3 | 216 | 4.0 | 0.04 | 0.004 |

What is claimed is:

1. A nanoparticle comprising:
   (a) a nanoshell comprising a potato protein; and (b) a core comprising a vitamin, said vitamin is bound to said potato protein; and said vitamin is encapsulated by said nanoshell, said potato protein comprises patatin,
   wherein a concentration ratio of said vitamin to said potato protein is 20:1 to 1:20,
   wherein said nanoparticle is adapted:
   (a) to be dissolved within an aqueous solution at a concentration of 0.1 microgram/ml to 1 mg/ml; and
   (b) not to affect the transparency of said aqueous solution.

2. The nanoparticle of claim 1, wherein said vitamin is a compound having maximal aqueous solubility below 1 g/l in its free form.

3. The nanoparticle of claim 1, wherein said vitamin is: vitamin D, vitamin E, vitamin A, or vitamin K, or any combination thereof.

4. The nanoparticle of claim 1, having a diameter of 10 nm to 100 nm.

5. The nanoparticle of claim 1, wherein said potato protein is made from a potato protein isolate having over 90% crude protein weight per dry weight.

6. A transparent beverage comprising the aqueous liquid and the nanoparticle of claim 1.

7. The transparent beverage of claim 6, stable for at least 60 seconds at pH 2.5 and a temperature of 72° C.

8. The transparent beverage of claim 6, wherein said vitamin is present at a concentration of 0.1 microgram/ml to 1 mg/ml.

9. The transparent beverage of claim 6, further comprising a bioactive compound selected from the group consisting of: an oil-soluble vitamin, a polyunsaturated fatty acid or its ester, an antioxidant, an Omega-3 fatty acid, docosahexaenoic acid (DHA), an ester of DHA, eicosapentaenoic acid (EPA), an ester of EPA, a phytochemical, vitamin D, vitamin E, vitamin A, or vitamin K, or any combination thereof.

10. A method of supplementing a subject with a vitamin, comprising the step of administering to said subject the transparent beverage of claim 6, thereby supplementing a subject with a bioactive compound.

11. The method of claim 10, wherein said transparent beverage is in the form of a nano-emulsion or a nano-dispersion.

* * * * *